US011523844B2

(12) United States Patent
Sun et al.

(10) Patent No.: US 11,523,844 B2
(45) Date of Patent: Dec. 13, 2022

(54) FREELY-CONNECTABLE THREE-STRUT PARALLEL ORTHOPEDIC EXTERNAL FIXATOR

(71) Applicant: TIANJIN UNIVERSITY, Tianjin (CN)

(72) Inventors: Tao Sun, Tianjin (CN); Sida Liu, Tianjin (CN); Yimin Song, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 148 days.

(21) Appl. No.: 16/762,868

(22) PCT Filed: Aug. 28, 2018

(86) PCT No.: PCT/CN2018/102720
§ 371 (c)(1),
(2) Date: May 8, 2020

(87) PCT Pub. No.: WO2019/184227
PCT Pub. Date: Oct. 3, 2019

(65) Prior Publication Data
US 2021/0000508 A1 Jan. 7, 2021

(30) Foreign Application Priority Data

Mar. 26, 2018 (CN) .......................... 201810253067.4

(51) Int. Cl.
*A61B 17/62* (2006.01)
*A61B 17/88* (2006.01)
(Continued)

(52) U.S. Cl.
CPC .............. *A61B 17/62* (2013.01); *A61B 17/88* (2013.01); *A61B 90/39* (2016.02); *A61B 17/90* (2021.08); *A61B 2090/3937* (2016.02)

(58) Field of Classification Search
CPC ....... A61B 17/62; A61B 17/60; A61B 17/603; A61B 17/64; A61B 17/88; A61B 17/90;
(Continued)

(56) References Cited

U.S. PATENT DOCUMENTS 4,979,348 A    12/1990  Perobelli et al.
5,074,866 A *  12/1991  Sherman ................ A61B 17/62
                                                606/56
(Continued)

FOREIGN PATENT DOCUMENTS

CN      202235624 U    5/2012
CN      107693096 A    2/2018
(Continued)

OTHER PUBLICATIONS

International Search Report of PCT/CN2018/102720.
Written Opinion of PCT/CN2018/102720.

*Primary Examiner* — Jan Christopher L Merene
*Assistant Examiner* — Anna V. Little
(74) *Attorney, Agent, or Firm* — Dragon Sun Law Firm, PC; Jinggao Li; Nathaniel Perkins

(57) ABSTRACT

A freely-connectable three-strut parallel orthopedic external fixator including two fixation rings and three struts, connecting holes are circumferentially and uniformly distributed on the ring surfaces of each fixation ring, each strut is provided with two driving translational pairs, a revolute pair and a spherical pair. Two fixation rings are respectively fixedly connected with the bone segments of the fracture site by using medical metal bone pins; adjusting the driving translational pairs of the six struts can achieve six DoF relative movement of the two fixation rings, thereby achieving fracture reduction. The external fixator of the present invention realizes free connection between the two fixation rings, which facilitates fixator installment; number of struts is less than the existing external fixators.

12 Claims, 7 Drawing Sheets

(51) Int. Cl.
   *A61B 90/00*    (2016.01)
   *A61B 17/90*    (2006.01)
(58) Field of Classification Search
   CPC .. A61B 2017/00991; A61B 2017/3937; A61B 17/7077; A61B 17/7079; A61B 17/708; A61B 17/7082; A61B 17/0206; A61B 2017/603
   See application file for complete search history.

(56) References Cited

U.S. PATENT DOCUMENTS

| | | | | |
|---|---|---|---|---|
| 6,030,386 | A * | 2/2000 | Taylor | A61B 17/62 606/56 |
| 9,044,271 | B2 | 6/2015 | Edelhauser et al. | |
| 2010/0234844 | A1* | 9/2010 | Edelhauser | A61B 17/62 606/56 |
| 2012/0303029 | A1* | 11/2012 | Vasta | A61B 17/60 606/56 |
| 2014/0135764 | A1* | 5/2014 | Ross | A61B 17/66 606/57 |
| 2015/0272624 | A1* | 10/2015 | Singh | A61B 17/62 606/56 |
| 2016/0000465 | A1* | 1/2016 | Ross | A61B 17/62 606/56 |
| 2016/0235444 | A1* | 8/2016 | Crozet | A61B 17/88 |
| 2017/0354439 | A1* | 12/2017 | Mannanal | A61B 17/66 |

FOREIGN PATENT DOCUMENTS

| | | |
|---|---|---|
| WO | 2011163406 A2 | 12/2011 |
| WO | 2019184227 A1 | 10/2019 |

* cited by examiner

FREELY-CONNECTABLE THREE-STRUT PARALLEL ORTHOPEDIC EXTERNAL FIXATOR

CROSS-REFERENCE TO RELATED APPLICATIONS

This application is a national stage application of PCT Application No. PCT/CN2018/102720. This application claims priority from PCT Application No. PCT/CN2018/102720, filed Aug. 28, 2018, CN Application No. CN 201810253067.4, filed Mar. 26, 2018, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

FIELD OF THE INVENTION

The present invention relates to the technical field of orthopedic external fixation, in particular to a six-degree-of-freedom parallel external fixator consisting of three struts and two fixation rings, with the struts which are freely connectable.

BACKGROUND OF THE INVENTION

The orthopedic external fixator can percutaneously fix the fracture ends through minimally invasive therapy by using external bone fixation pins, which can realize effective fixation of fracture sites and can provide a function of adjusting bone segments in a certain degree of freedom (hereinafter referred to as DoF). At present, orthopedic external fixator and related technology have been applied to traumatic fracture reduction and bone deformity correction.

U.S. Pat. No. 4,979,348A discloses a parallel external fixator consisting of two fixation rings and a plurality of longitudinally parallel connected threaded rods between the two fixation rings. The threaded rods insert through the connecting holes of the fixation rings, and relative translation movement or fixation of the fixation rings can be realized by nuts mounted on the threaded rods. The fixator has a simple structure, and has better stability than the general unilateral external fixator. However, the adjustable DoF is limited and it is difficult to achieve the reduction of spatial fracture deformity.

U.S. Pat. No. 6,030,386A and patent WO2011163406A2 provide a class of parallel external fixators, each of which consists of six struts with the same topological structure and two fixation rings. The operator uses external bone fixation pins to fixedly connect the two fixation rings with the fracture segments of a patient; and the six struts are connected to the two fixation rings through hinges at both ends. Adjusting the lengths of the six struts can achieve six DoFs relative movement of the two fixation rings, thereby achieving fracture reduction; and after fracture reduction is completed, struts adjusting is stopped, and the external fixator maintains the relative stability of the fracture segments. This kind of external fixators can achieve the reduction of spatial fracture deformity, but it requires the six struts to be circumferentially and symmetrically configured, which are likely to interfere with the connecting parts of the external bone fixation pins. When taking fluoroscopic images to diagnose the fracture condition, the six struts cover the fracture sites and affect the observation at times; and moreover, the weight of such fixators are large, making it uneasy for long-term wearing by the patient for post operative rehabilitation.

U.S. Pat. No. 9,044,271B2 provides a three-strut parallel external fixator. Each strut consists of two worm-and-gear kinematic pairs, one revolute kinematic pair and one spherical kinematic pair. The two worm-and-gear kinematic pairs of each strut are driving joints. Although this kind of external fixators has fewer struts, the gear tooth edge employed by the external fixation rings requires a complex manufacturing, the worm-and-gear structure has a large weight, and it is difficult to guarantee the accuracy. In addition, the driving joints are difficult to accurately read and adjust, thus having poor practicability.

Therefore, a heretofore unaddressed need exists in the art to address the aforementioned deficiencies and inadequacies.

SUMMARY OF THE INVENTION

The purpose of the present invention is to overcome the shortcomings of the existing parallel external fixator, and to provide a six DoFs parallel external fixator consisting of three struts and two fixation rings, which has the advantages that the struts are freely connectable, the weight is light, the accuracy is high and the interference on fluoroscopic images is low.

The present invention is implemented through the following technical solution.

The freely-connectable three-strut parallel orthopedic external fixator provided by the present invention comprises a distal fixation ring and a proximal fixation ring set above the distal fixation ring, the proximal fixation ring and the distal fixation ring have the same structure, connecting holes are circumferentially and uniformly distributed in the ring surfaces of the proximal fixation ring and the distal fixation ring, three struts with the same topological structure are uniformly distributed between the proximal fixation ring and the distal fixation ring, each strut comprises a first driving joint and a second driving joint, the first driving joint comprises a guide rail, two ends of the guide rail are connected with the connecting holes in the proximal fixation ring through bolts and nuts, a first sliding groove is provided in the middle of the guide rail and along the length direction of the guide rail, lugs are provided on the two sides of the guide rail, and two ends of a lead screw provided along the same direction as the first sliding groove are rotatably connected with the connecting holes in the lugs, the lead screw is in threaded connection with a slider, a part of the slider is provided in the first sliding groove and is capable of sliding in the first sliding groove, the guide rail, the slider and the lead screw jointly form a first translational pair, a first scale mark is provided on the guide rail, a first indicating mark is provided on the slider, the driving displacement value of the first driving joint is read through the position indicated by the first indicating mark and the first scale mark, while rotating the first lead screw is capable of adjusting the displacement value of the first translational pair so as to realize first active drive; the motion axis of the first active drive is along the axis direction of the lead screw, the second driving joint comprises a first rotary connecting rod, the head part of a screw rod and the lower part of the first rotary connecting rod, which are in threaded connection with each other, are locked through a nut to eliminate gap, the middle part of the screw rod and one end of a driving nut form a screw pair, and the other end of the screw rod inserts into a cavity of a sliding sleeve; a pin is fixed at the other end of the screw rod, the other end of the driving nut and one end of the sliding sleeve form a revolute pair, a second sliding groove is provided on the side of the sliding sleeve and along the axis direction of the sliding sleeve, the pin is capable of sliding in the second sliding groove through the movement of the sliding sleeve, a second scale mark is provided on the edge of one side of the second sliding groove, a second indicating mark is provided on the pin, the displacement value of the second driving joint is read through the position indicated by the second indicating mark on the second scale mark, the screw rod, the driving nut and the sliding sleeve jointly form a second translational pair, and rotating the driving nut is capable of adjusting the displacement value of the second translational pair to realize second active drive; the motion axis of the second active drive is along the axis direction of the screw rod, and the movement direction of the first translational pair and the movement direction of the second translational pair are configured to be perpendicular to each other; the head part of the rotary connecting rod is rotatably connected with the slider through a first pin shaft, the first rotary connecting rod and the slider form a first revolute pair, the axis of the first pin shaft and the axis of the lead screw are configured to be in parallel, and the bottom part of the sliding sleeve is rotatably connected with one end of a universal hinge with a cross shaft component through a second revolute pair such that one end of the universal hinge has one rotational DoF relative to the sliding sleeve; the rotation axis of the second revolute pair coincides with the axis of the sliding sleeve, the universal hinge contains a cross shaft component such that the two ends of the universal hinge have two rotational DoFs therebetween, the other end of the universal hinge is connected to a second pin shaft having an external thread, and the second pin shaft is fixedly connected with the connecting hole in the distal fixation ring through a nut.

Another implementation of the freely-connectable three-strut parallel orthopedic external fixator, comprises a distal fixation ring and a proximal fixation ring set above the distal fixation ring, the proximal fixation ring and the distal fixation ring have the same structure, connecting holes are circumferentially and uniformly distributed in the ring surfaces of the proximal fixation ring and the distal fixation ring, three struts with the same topological structure are uniformly distributed between the proximal fixation ring and the distal fixation ring, the first driving joint comprises a guide rail, the both ends of the guide rail are connected with the connecting holes in the proximal fixation ring through bolts and nuts, a first sliding groove is provided in the middle of the guide rail and along the length direction of the guide rail, a lead screw provided along the same direction as a first sliding groove is mounted in the first sliding groove of the guide rail, the two ends of the lead screw are rotatably connected with the connecting holes in the left and right ends of the first sliding groove, the lead screw is in threaded connection with a slider, the upper portion of the slider is inserted in the first sliding groove and is capable of sliding in the first sliding groove, the guide rail, the slider and the lead screw jointly form a first translational pair, a first scale mark is provided on the guide rail, a first indicating mark is provided on the slider, and the driving displacement value of the first driving joint is read through the position indicated by the first indicating mark and the first scale mark; the second driving joint comprises a spherical hinge, the lower portion of the slider is fixedly connected with the shaft at the upper end of the spherical hinge, the shaft at the upper end of the spherical hinge is perpendicular to the movement direction of the first translational pair, the upper end of a screw rod and the lower end of the spherical hinge, which are in threaded connection with each other, are locked through a nut to eliminate gap, and the spherical hinge provides three rotational DoFs between the first driving joint and the second driving joint so as to form a second spherical pair; the middle part of the screw rod and one end of a driving nut form a screw pair, the other end of the screw rod inserts into a cavity of a sliding sleeve, a pin is fixed on the lower end of the screw rod, the other end of the driving nut and the sliding sleeve form a revolute pair, a second sliding groove is provided on the side of the sliding sleeve along the axis direction, the pin is capable of sliding in the second sliding groove through the movement of the sliding sleeve, a second scale mark is provided on the edge of one side of the second sliding groove, a second indicating mark is provided on the pin, the displacement value of the second driving joint is read through the position indicated by the second indicating mark on the second scale mark, the screw rod, the driving nut and the sliding sleeve jointly form a second translational pair, the movement direction of the first translational pair and the movement direction of the second translational pair are configured to intersect with each other, the lower end of the sliding sleeve is fixedly connected with one end of a second rotary connecting rod, the other end of the second rotary connecting rod is rotatably connected with a connecting seat through a third pin shaft to form a third revolute pair, the rotation axis of the third revolute pair and the axis of the sliding sleeve are configured to be perpendicular to each other, and the connecting seat is fixedly connected with the connecting hole in the distal fixation ring through a bolt and a nut.

The present invention has the following beneficial effects.

(1) Six-DoF fracture reduction is realized by using fewer struts, the weight of the external fixator is lighter, and the interference on the observation of fluoroscopic images is reduced.

(2) It is easy to manufacture and realize the structure of the struts, there are fewer restrictions on the mounting of the struts, asymmetric mounting can be realized, and the interference with bone pin fixing components is effectively avoided.

(3) Since the translational pair which can accurately indicate the position is selected as the driving joint of the struts, the reduction accuracy of the external fixator is effectively improved.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE EMBODIMENTS

Figure 1:
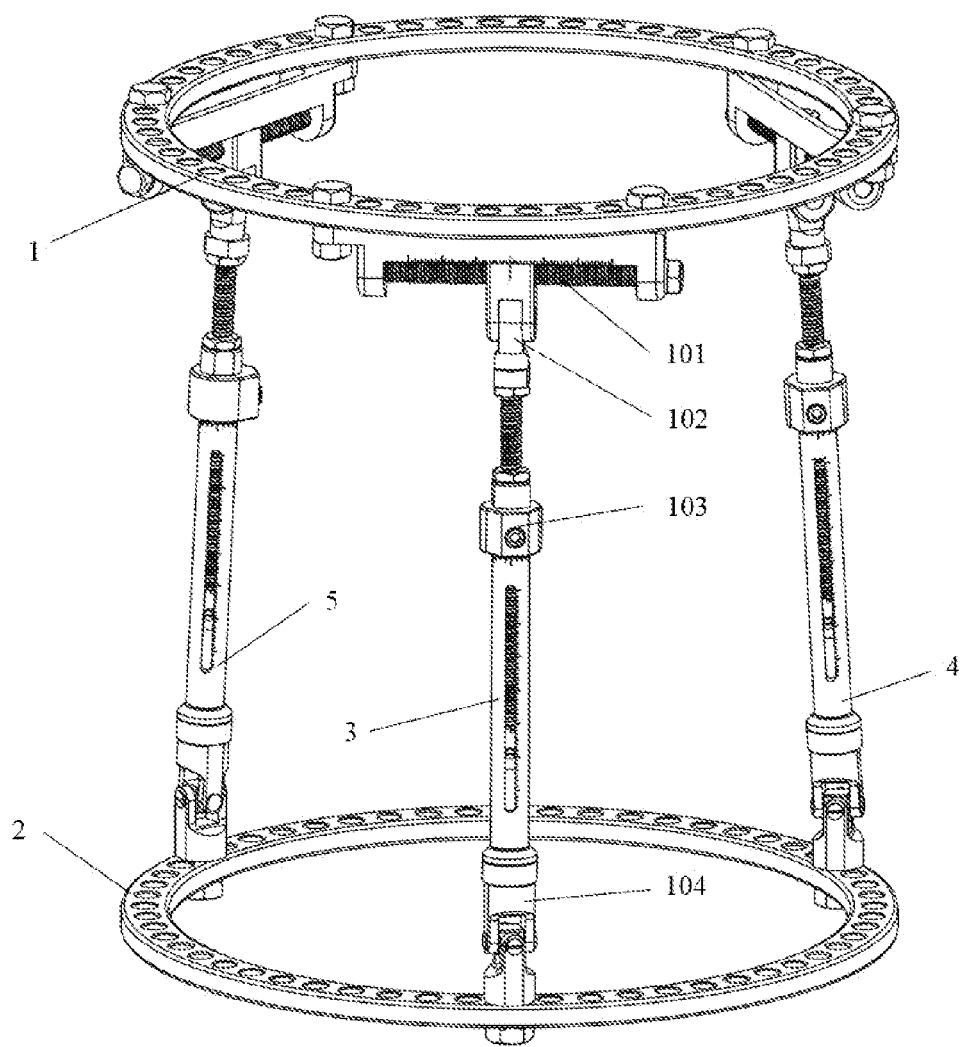
FIG. 1 illustrates a schematic view of a first embodiment of a freely-connectable three-strut parallel orthopedic external fixator provided by the present invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout. The specific embodiments of the present invention will be described below in detail with reference to the drawings.

Figures 2, 3, 4:
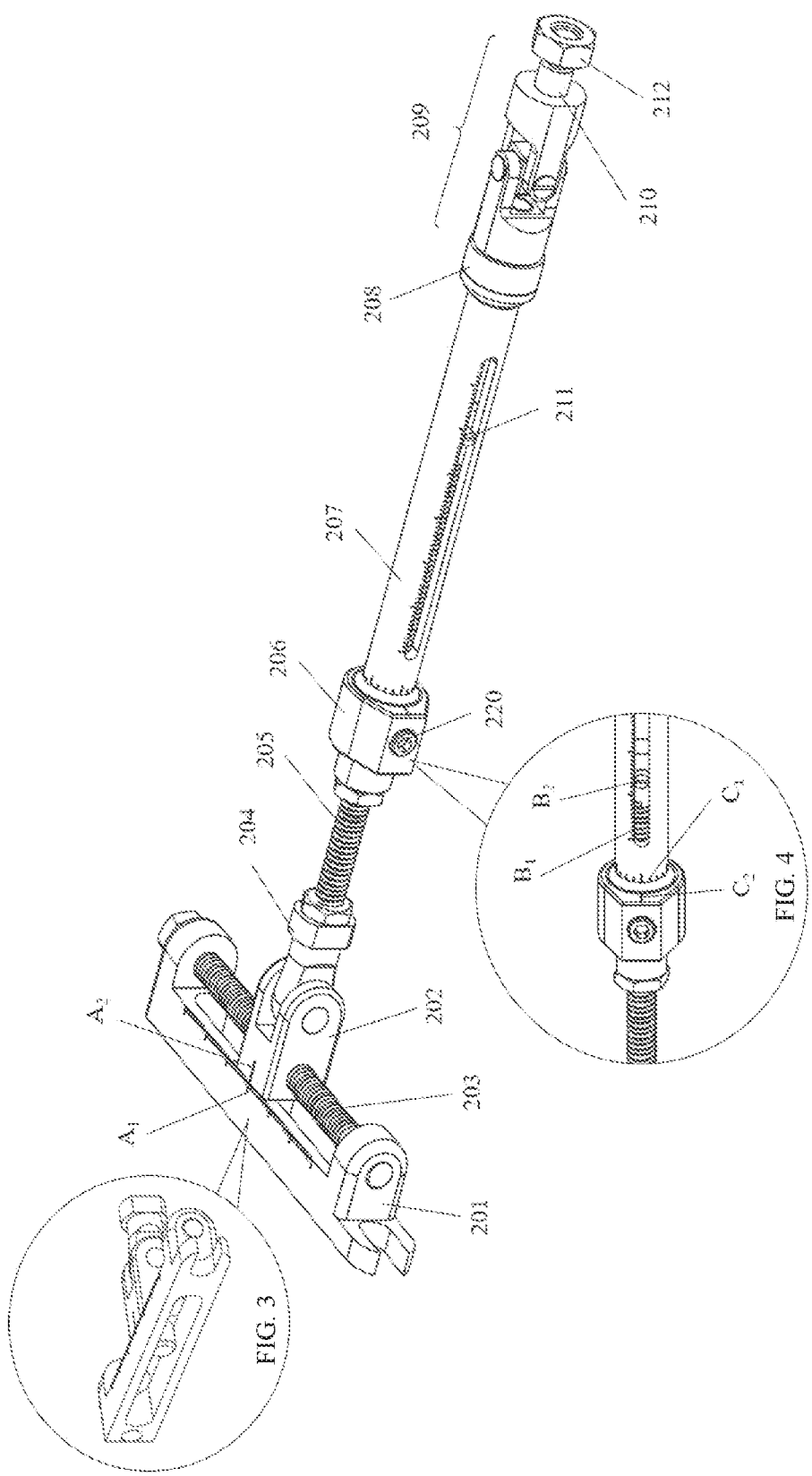
FIG. 2 illustrates a structural schematic view of a strut of the external fixator illustrated in FIG. 1.
FIG. 3 illustrates a top view of a first driving joint of the strut illustrated in FIG. 2.
FIG. 4 illustrates a front view of a second driving joint of the strut illustrated in FIG. 2.
Figure 3:
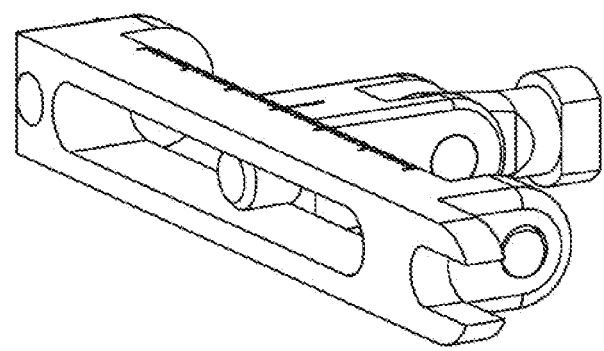
Figure 4:
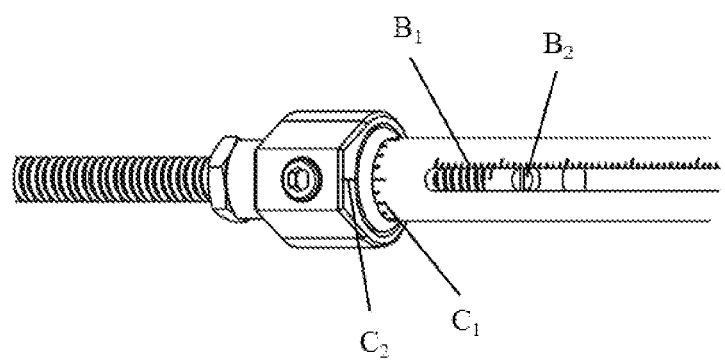

As illustrated in the drawings, the freely-connectable three-strut parallel orthopedic external fixator provided by the present invention comprises a distal fixation ring 2 and a proximal fixation ring 1 set above the distal fixation ring, the proximal fixation ring 1 and the distal fixation ring 2 have the same structure, and connecting holes are circumferentially and uniformly distributed in the ring surfaces of the proximal fixation ring 1 and the distal fixation ring 1. Three struts with the same topological structure are uniformly distributed between the proximal fixation ring 1 and the distal fixation ring 2, which are respectively a first strut 3, a second strut 4 and a third strut 5, as illustrated in FIG. 1 and FIG. 2. Each strut comprises a first driving joint and a second driving joint.

Figure 5:
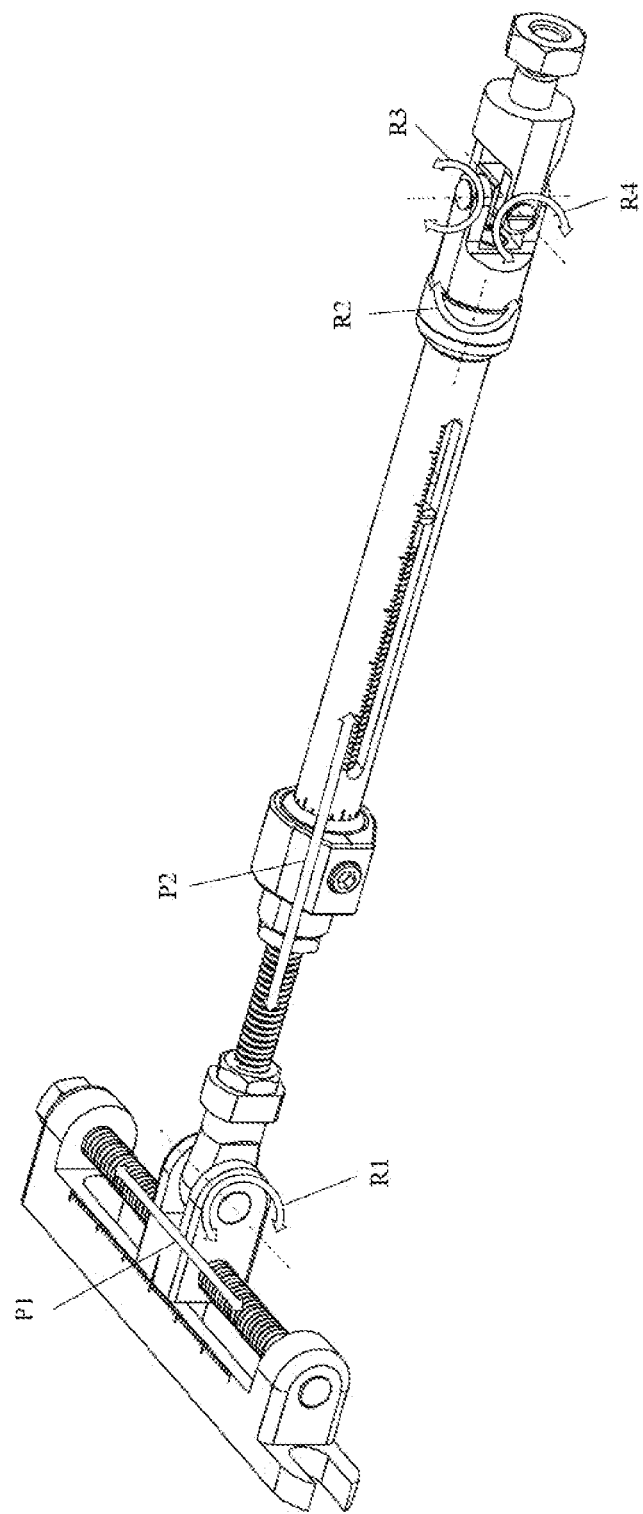
FIG. 5 illustrates a schematic view of movement degrees of freedom of the strut illustrated in FIG. 2.

As a first embodiment of the present invention, as illustrated in FIG. 2, the first driving joint comprises a guide rail 201, the two ends of the guide rail are connected with the connecting holes in the proximal fixation ring 1 through bolts and nuts, a first sliding groove is provided in the middle of the guide rail 201 along the length direction, lugs are provided on the two sides of the guide rail 201, and the two ends of a lead screw 203 provided along the same direction as the first sliding groove are rotatably connected with the connecting holes in the lugs. The lead screw 203 is in threaded connection with a slider 202. A part of the slider 202 is provided in the first sliding groove and is capable of sliding in the first sliding groove, and the guide rail 201, the slider 202 and the lead screw 203 jointly form the first translational pair 101. A first scale mark $A_1$ is provided on the guide rail 201 and a first indicating mark $A_2$ is provided on the slider. The driving displacement value of the first driving joint is read through the position indicated by the first indicating mark $A_2$ and the first scale mark $A_1$. Rotating (which may be performed manually) the first lead screw 203 is capable of adjusting the displacement value of the first translational pair 101 so as to realize first active drive; and the motion axis of the first active drive is along the axis direction of the lead screw 203. As illustrated in FIG. 5, the first translational pair 101 has one translation DoF P1.

The second driving joint comprises a first rotary connecting rod 204, the head part of a screw rod 205 and the lower part of the first rotary connecting rod 204, which are in threaded connection with each other, are locked through a nut to eliminate gap. The middle part of the screw rod 205 and one end of a driving nut 206 form a screw pair, and the bottom part of the screw rod 205 inserts into a cavity of a sliding sleeve 207; and a pin 211 is fixed at the other end of the screw rod 205. The other end of the driving nut 206 and the head part of the sliding sleeve 207 form a revolute pair, a second sliding groove is provided on the side of the sliding sleeve 207 along the axis direction, and the pin 211 is capable of sliding in the second sliding groove through the movement of the sliding sleeve 207. A second scale mark $B_1$ is provided on the edge of one side of the second sliding groove, a second indicating mark $B_2$ is provided on the pin 211, and the displacement value of the second driving joint is read through the position indicated by the second indicating mark $B_2$ and the second scale mark $B_1$. The screw rod 205, the driving nut 206 and the sliding sleeve 207 jointly form a second translational pair 103. Rotating (which may be performed manually) the driving nut 206 is capable of adjusting the displacement of the second translational pair 103 to realize second active drive; and the motion axis of the second driving joint is along the axis direction of the screw rod 205. As illustrated in FIG. 5, the second translational pair 103 has one translational DoF P2. The movement direction of the first translational pair and the movement direction of the second translational pair are configured to be perpendicular to each other.

The head part of the first rotary connecting rod 204 is connected with the slider 202 through a first pin shaft, and the rotary connecting rod and the slider form a first revolute pair 102. The axis of the first pin shaft and the axis of the lead screw are configured to be in parallel. As illustrated in FIG. 5, the first revolute pair 102 has a rotational DoF R1 along the axis of the first pin shaft, the bottom part of the sliding sleeve 207 is rotatably connected with one end of a universal hinge 209 with a cross shaft component through a second revolute pair 208 such that one end of the universal hinge 209 has one rotational DoF R2 relative to the sliding sleeve 207; and the rotation axis of the second revolute pair 208 coincides with the axis of the sliding sleeve 207. The universal hinge 209 has a cross shaft component such that the two ends of the universal hinge have two rotational DoFs therebetween, respectively R3 and R4; and the other end of the universal hinge is connected to a second pin shaft 210 having an external thread, and the second pin shaft is fixedly connected with the connecting hole in the distal fixation ring 2 through a nut 212. As illustrated in FIG. 2 and FIG. 5, the second revolute pair 208 and the universal hinge 209 provide three rotational DoFs between the sliding sleeve 207 and the distal fixation ring 2 to form a first spherical pair 104 (the three rotational DoFs are respectively rotational DoF R2 of the second revolute pair 208 along the axis of the sliding sleeve, and two rotational DoFs R3 and R4 of the universal hinge itself). The first spherical pair 104, the second translational pair 103, the first revolute pair 102 and the first translational pair 101 provide six independent DoFs (rotational DoFs R1, R2, R3, and R4, and translational DoFs P1, and P2).

Figure 6:
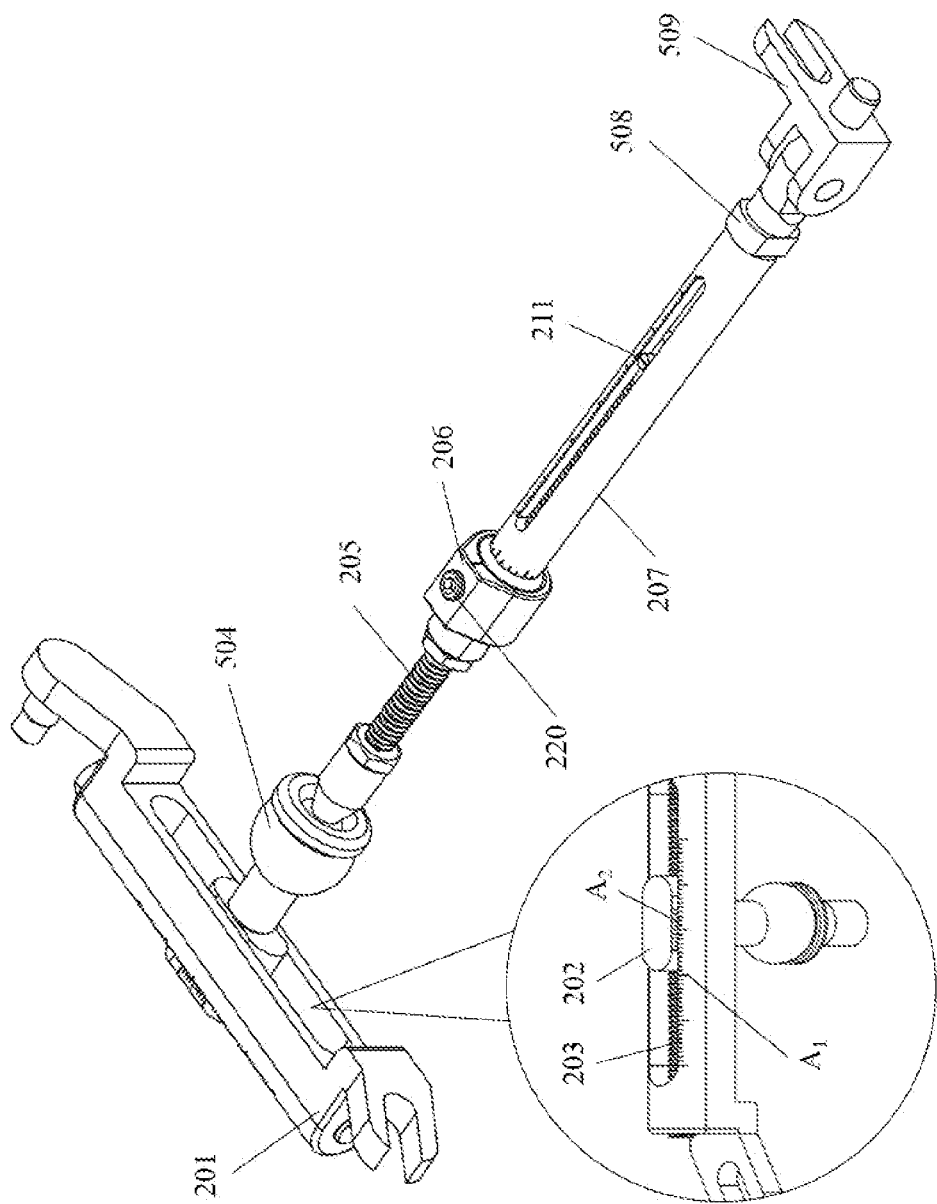
FIG. 6 illustrates a structural schematic view of the strut according to the second embodiment of the present invention; the enlarged detailed view illustrates a top view of the first driving joint of the strut illustrated in FIG. 6.

As a second embodiment of the present invention, as illustrated in FIG. 6, the topological structure of the struts are substantially the same as the struts in the first embodiment, and the way of structural movement may refer to the first embodiment. The first driving joint comprises a guide rail 201, the two ends of the guide rail 201 are connected with the connecting holes in the proximal fixation ring 1 through bolts and nuts, a first sliding groove is provided in the middle of the guide rail 201 and along the length direction of the guide rail 201, a lead screw 203 provided along the same direction as a first sliding groove is mounted in the first sliding groove of the guide rail 201, the two ends of the lead screw 203 are rotatably connected with the connecting holes in the left and right ends of the first sliding groove, and the lead screw 203 is in threaded connection with a slider 202. The upper portion of the slider 202 is inserted in the first sliding groove and is capable of sliding in the first sliding groove. The guide rail 201, the slider 202 and the lead screw 203 jointly form a first translational pair 101. A first scale mark $A_1$ is provided on the guide rail 201, and a first indicating mark $A_2$ is provided on the slider. The driving displacement value of the first driving joint is read through the position indicated by the first indicating mark Aland the first scale mark $A_1$.

The second driving joint comprises a spherical hinge 504, and the lower portion of the slider 202 is fixedly connected with the shaft at the upper end of the spherical hinge 504. The shaft at the upper end of the spherical hinge 504 is perpendicular to the movement direction of the first translational pair, the upper end of a screw rod 205 and the lower end of the spherical hinge 504, which are in threaded connection with each other, are locked through a nut to eliminate gap. The spherical hinge 504 provides three rotational DoFs between the first driving joint and the second driving joint so as to form a second spherical pair 701.

The middle part of the screw rod 205 and one end of a driving nut 206 form a screw pair, and the lower end of the screw rod 205 inserts into a cavity of a sliding sleeve 207; and a pin 211 is fixed on the other lower of the screw rod 205. The other end of the driving nut 206 and the sliding sleeve 207 form a revolute pair, a second sliding groove is provided on the side of the sliding sleeve 207 along the axis direction, and the pin 211 is capable of sliding in the second sliding groove through the movement of the sliding sleeve 207. A second scale mark $B_1$ is provided on the edge of one side of the second sliding groove, a second indicating mark $B_2$ is provided on the pin, and the displacement value of the second driving joint is read through the position indicated by the second indicating mark $B_2$ on the second scale mark $B_1$. The screw rod 205, the driving nut 206 and the sliding sleeve 207 jointly form a second translational pair 103. The movement direction of the first translational pair and the movement direction of the second translational pair are configured to intersect with each other.

The lower end of the sliding sleeve 207 is fixedly connected with one end of a second rotary connecting rod 508, and the other end of the second rotary connecting rod 508 is rotatably connected with a connecting seat 509 through a third pin shaft to form a third revolute pair 702. The rotation axis of the third revolute pair and the axis of the sliding sleeve are configured to be perpendicular to each other. As illustrated in FIG. 6, the two ends of the guide rails of three struts 3, 4 and 5 are respectively fixedly connected with the connecting holes in the proximal fixation ring 1 through bolts and nuts, and the connecting seat 509 at the lower portion of the strut is fixedly connected with the connecting hole in the distal fixation ring 2 through a bolt and a nut, such that the mounting of the external fixator can be completed.

Figure 7:
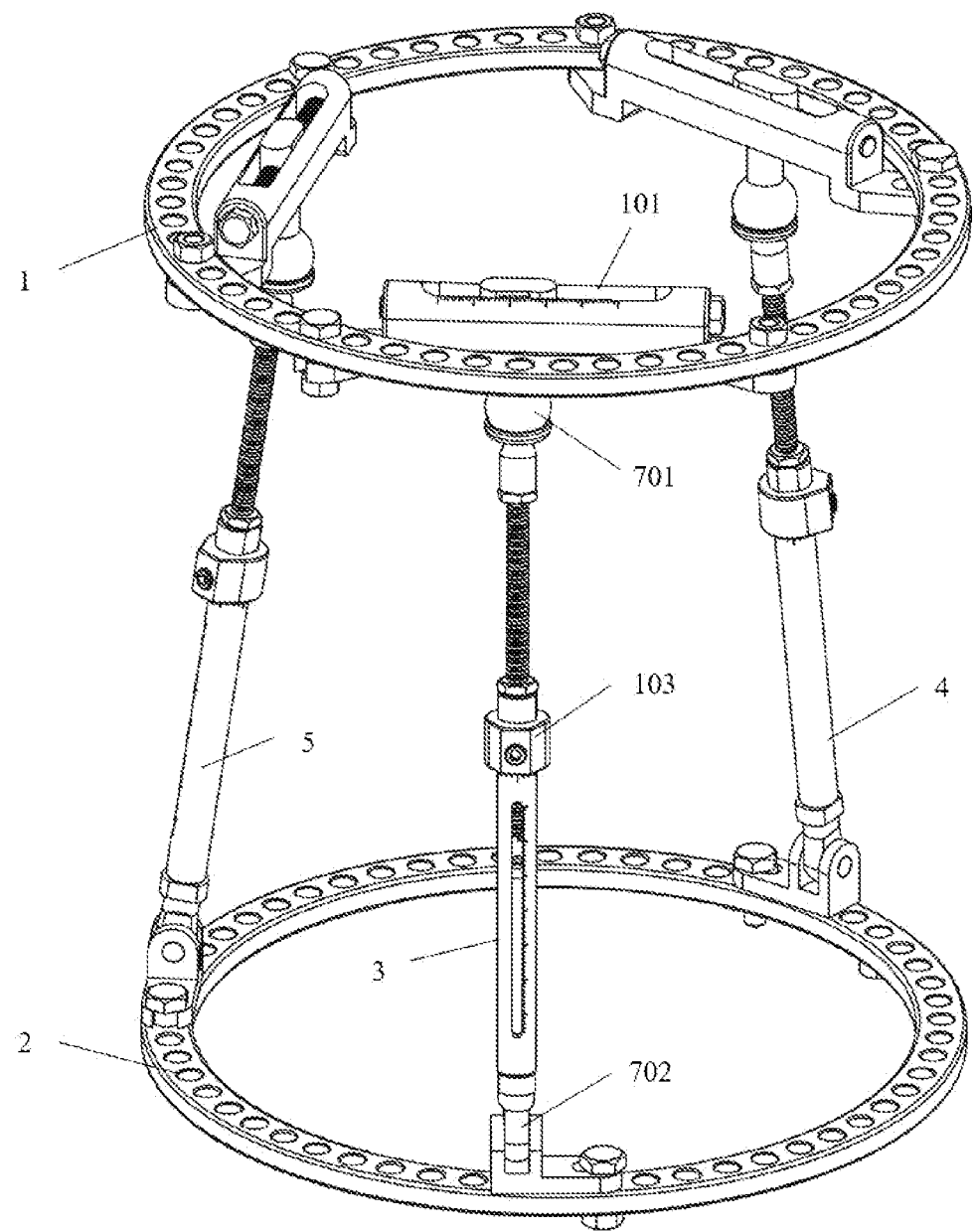
FIG. 7 illustrates a structural schematic view of an external fixator formed by mounting the struts illustrated in FIG. 6.

Preferably, the first scale mark $A_1$ of the guide rail 201 and the first indicating mark $A_2$ of the slider 202 are configured in the form of caliper as illustrated in FIG. 7. Wherein, the first scale mark $A_1$ corresponds to the main scale of the caliper, and the first indicating mark $A_2$ corresponds to the auxiliary scale of the caliper. This form can more accurately indicate the driving displacement value of the first driving joint.

Preferably, the sliding sleeve 207 is provided with third scale marks $C_1$ which are circumferentially spaced apart at the same angular intervals, and a third indicating mark $C_2$ is provided on the driving nut 206, as illustrated in FIG. 4. When the driving nut 206 is rotated, the position indicated by the third indicating mark $C_2$ on the third scale marks $C_1$ continuously varies with the rotation angle of the driving nut 206, and the rotation amount $\alpha$ ($0 \leq \alpha \leq 360°$) of the driving nut 206 may be read. The displacement value of the second driving joint can be read more accurately according to the following formula:

$$P_2 = l_2 + \alpha \cdot P_h / 360°$$

where $P_2$ represents the displacement value of the second driving joint, $l_2$ represents the displacement value of the second driving joint by rounding down the reading made by the second scale mark $B_1$ and the second indicating mark $B_2$ of the second driving joint, $P_h$ represents the thread lead of screw rod 205, and $\alpha$ represents the rotation amount of the driving nut. Adopting the above functional structures can improve the fixation reliability of the fracture ends and significantly improve the positioning accuracy of the external fixator.

Preferably, the driving nut 206 is provided with a locking screw 220, the locking screw 220 may be provided pressing against the sliding sleeve, the operator tightens the locking screw 220 such that the relative rotation of the driving nut 206 and the sliding sleeve 207 can be restricted to realize the locking of the second driving joint, thus the misoperation of adjusting the second driving joint unwillingly can be avoided when the external fixator is fixing on the fracture segments.

Figure 8:
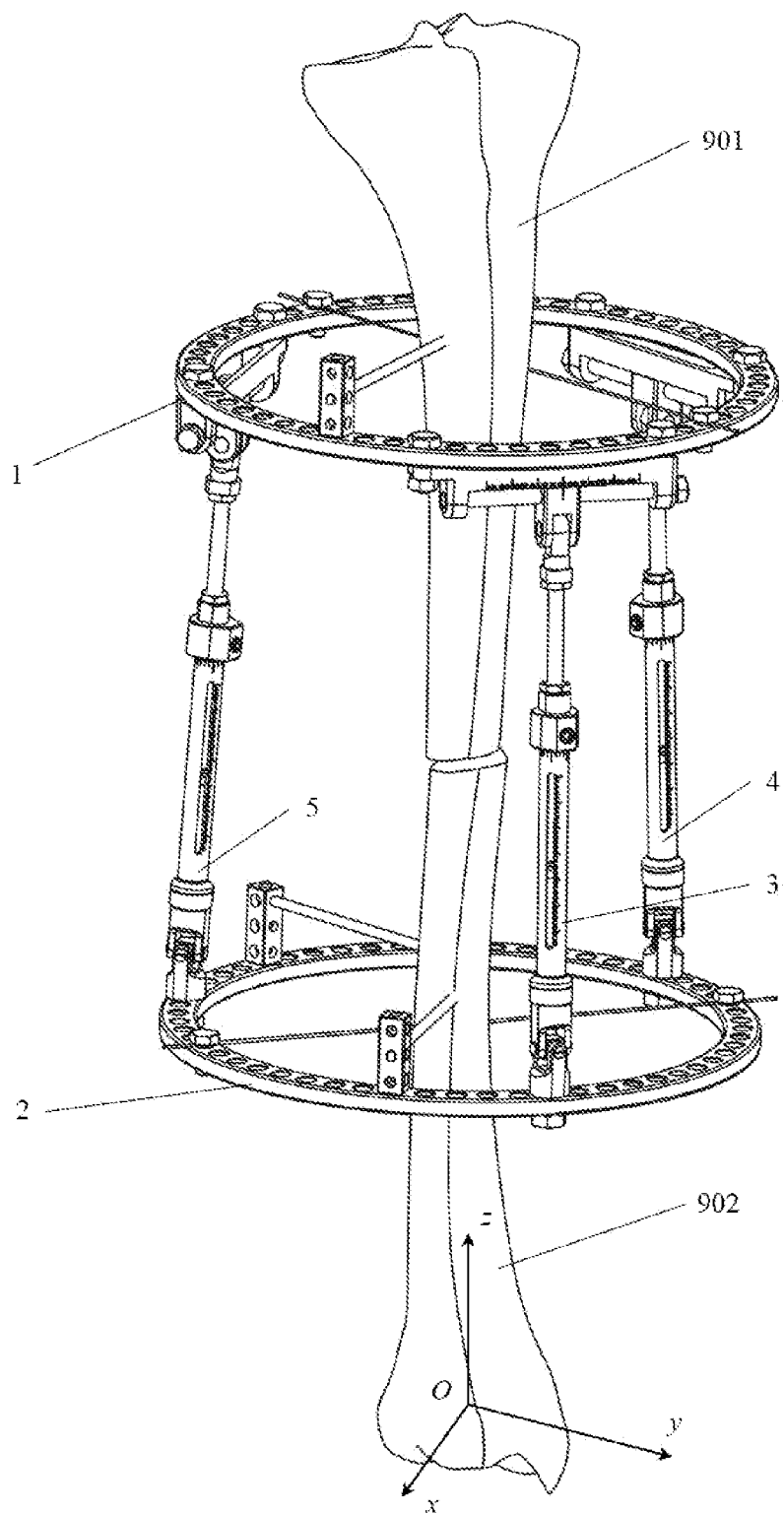
FIG. 8 illustrates a schematic view of the use effect of the external fixator provided by the present invention.

When using the external fixator provided by the present invention, the proximal fixation ring 1 and the distal fixation ring 2 are respectively fixedly connected with a proximal bone segment 901 and a distal bone segment 902 at the two sides of the fracture ends by using medical metal bone pins and pin fixation components, and then the two ends of the guide rails at the upper portions of the first strut 3, the second strut 4 and the third strut 5 are respectively fixedly connected with the connecting holes in the proximal fixation ring 1 by using bolts and nuts, the connecting seats at the lower portions of the three struts are fixedly connected with the connecting holes in the distal fixation ring 2 by using bolts and nuts to complete the mounting of the external fixator (see FIG. 8) to realize the effective fixation of the fracture site.

Under the first implemented structure or the second implemented structure, the first driving joint and the second driving joint of each of the first strut 3, the second strut 4 and the third strut 5 are adjusted according to certain rules, the proximal fixation ring 1 realize three-dimensional translation movement along the spatial coordinate axes $\overrightarrow{Ox}$, $\overrightarrow{Oy}$ and $\overrightarrow{Oz}$ relative to the distal fixation ring 2 (as illustrated in FIG. 9) and realize three-dimensional rotation movement around the spatial coordinate axes $\overrightarrow{Ox}$, $\overrightarrow{Oy}$ and $\overrightarrow{Oz}$. The relative movement in space can effectively adjust the relative position and posture of the proximal bone segment 901 and the distal bone segment 902 to realize fracture reduction.

The above description of the present invention is only illustrative rather than restrictive. Therefore, the embodiments of the present invention are not limited to the specific embodiments described above. Similarly, under the inspiration of the mechanical structure of the present invention, other changes in the configuration of the translational pairs or variations of the mechanical structure made without departing from the spirit of the present invention and the scope claimed by the claims shall all fall into the protection scope of the present invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A freely-connectable three-strut parallel orthopedic external fixator, including a distal fixation ring and a proximal fixation ring above the distal fixation ring, the proximal fixation ring and the distal fixation ring have the same structure, connecting holes are circumferentially and uniformly distributed in ring surfaces of the proximal fixation ring and the distal fixation ring, three struts with the same topological structure are uniformly distributed between the proximal fixation ring and the distal fixation ring, each strut comprises a first driving joint and a second driving joint, the first driving joint comprises a guide rail, two ends of the guide rail are connected with a first and a second connecting hole of the connecting holes in the proximal fixation ring through bolts and nuts, a first sliding groove is provided in a middle of the guide rail and along a length direction of the guide rail, lugs are provided on two sides of the guide rail, and two ends of a lead screw provided along the same direction as the first sliding groove are rotatably connected with holes in the lugs, the lead screw is in threaded connection with a slider, a part of the slider is provided in the first sliding groove and is capable of sliding in the first sliding groove; the guide rail, the slider and the lead screw jointly form a first translational pair, a first scale mark is provided on the guide rail, a first indicating mark is provided on the slider, a driving displacement value of the first driving joint is readable through the position indicated by the first indicating mark and the first scale mark, while rotating the first lead screw is capable of adjusting the driving displacement value of the first translational pair so as to realize first active drive; a motion axis of the first active drive is along an axis direction of the lead screw, the second driving joint comprises a first rotary connecting rod, a lower part of the first rotary connecting rod is in threaded connection with a head part of a screw rod, and both of which are locked through a nut to eliminate gap, a middle part of the screw rod and one end of a driving nut form a screw pair, and a bottom part of the screw rod inserts into a cavity of a sliding sleeve; a pin is fixed at another end of the screw rod, another end of the driving nut and a head part of the sliding sleeve form a revolute pair, a second sliding groove is provided on a side of the sliding sleeve along an axis direction, the pin is capable of sliding in the second sliding groove through the movement of the sliding sleeve, a second scale mark is provided on an edge of the second sliding groove, a second indicating mark is provided on the pin, a displacement value of the second driving joint is readable through the position indicated by the second indicating mark and the second scale mark, the screw rod, the driving nut and the sliding sleeve jointly form a second translational pair, and rotating the driving nut is capable of adjusting the displacement value of the second translational pair to realize second active drive; a motion axis of the second active drive is along an axis direction of the screw rod, and a movement direction of the first translational pair and a movement direction of the second translational pair are configured to be perpendicular to each other; a head part of the first rotary connecting rod is rotatably connected with the slider through a first pin shaft; the first rotary connecting rod and the slider form a first revolute pair, an axis of the first pin shaft and an axis of the lead screw are configured to be in parallel, and a bottom part of the sliding sleeve is rotatably connected with one end of a universal hinge with a cross shaft component, the sliding sleeve and the universal hinge form a second revolute pair providing one rotational degree of freedom (DoF); a rotation axis of the second revolute pair coincides with an axis of the sliding sleeve, the universal hinge contains a cross shaft component such that two ends of the universal hinge have two rotational DoFs therebetween, another end of the universal hinge is connected to a second pin shaft having an external thread, and the second pin shaft is fixedly connected with a connecting hole of the connecting holes in the distal fixation ring through a nut.

2. The freely-connectable three-strut parallel orthopedic external fixator according to claim 1, wherein the first scale mark of the guide rail and the first indicating mark of the slider are configured in the form of a caliper; wherein the first scale mark corresponds to a main scale of the caliper, and the first indicating mark corresponds to an auxiliary scale of the caliper.

3. The freely-connectable three-strut parallel orthopedic external fixator according to claim 1, wherein the sliding sleeve is provided with third scale marks which are circumferentially spaced apart at the same angular intervals, and a third indicating mark is provided on the driving nut; when rotating the driving nut, a position indicated by the third indicating mark on the third scale marks continuously varies with a rotation angle of the driving nut, and a rotation amount $\alpha$ of the driving nut is read, a value of $\alpha$ ranges $0 \leq \alpha \leq 360°$; the displacement value of the second driving joint is calculated according to the following formula:

$$P_2 = l_2 + \alpha \cdot P_h / 360°$$

where $P_2$ represents the displacement value of the second driving joint, $l_2$ represents the displacement value of the second driving joint by rounding down the reading made by the second scale mark and the second indicating mark, $P_h$ represents a thread lead of screw rod, and $\alpha$ represents the rotation amount of the driving nut.

4. The freely-connectable three-strut parallel orthopedic external fixator according to claim 3, wherein the driving nut is provided with a locking screw for pressing against the sliding sleeve.

5. A freely-connectable three-strut parallel orthopedic external fixator, including a distal fixation ring and a proximal fixation ring above the distal fixation ring, the proximal fixation ring and the distal fixation ring have the same structure, connecting holes are circumferentially and uniformly distributed in ring surfaces of the proximal fixation ring and the distal fixation ring, three struts with the same topological structure are uniformly distributed between the proximal fixation ring and the distal fixation ring, a first driving joint comprises a guide rail, the both ends of the guide rail are connected with a first and a second connecting hole of the connecting holes in the proximal fixation ring through bolts and nuts, a first sliding groove is provided in a middle of the guide rail and along a length direction of the guide rail, a lead screw provided along the same direction as a first sliding groove is mounted in the first sliding groove of the guide rail, two ends of the lead screw are rotatably connected with holes in the left and right ends of the first sliding groove, the lead screw is in threaded connection with a slider, an upper portion of the slider is inserted in the first sliding groove and is capable of sliding in the first sliding groove; the guide rail, the slider and the lead screw jointly form a first translational pair, a first scale mark is provided on the guide rail, a first indicating mark is provided on the slider, and a driving displacement value of the first driving joint is readable through a position indicated by the first indicating mark and the first scale mark; a second driving joint comprises a spherical hinge, a lower portion of the slider is fixedly connected with a shaft at an upper end of the spherical hinge, the shaft at the upper end of the spherical hinge is perpendicular to a movement direction of the first translational pair, an upper end of a screw rod and a lower end of the spherical hinge, which are in threaded connection with each other, are locked through a nut to eliminate gap, and the spherical hinge provides three rotational degrees of freedom (DoFs) between the first driving joint and the second driving joint so as to form a second spherical pair; a middle part of the screw rod and one end of a driving nut form a screw pair, a lower end of the screw rod inserts into a cavity of a sliding sleeve, a pin is fixed on a lower end of the screw rod, another end of the driving nut and the sliding sleeve form a revolute pair, a second sliding groove is provided on a side of the sliding sleeve along an axis direction, the pin is capable of sliding in the second sliding groove through a movement of the sliding sleeve, a second scale mark is provided on an edge of one side of the second sliding groove, a second indicating mark is provided on the pin, a displacement value of the second driving joint is readable through the position indicated by the second indicating mark and the second scale mark, the screw rod, the driving nut and the sliding sleeve jointly form a second translational pair, a movement direction of the first translational pair and a movement direction of the second translational pair are configured to intersect with each other, a lower end of the sliding sleeve is fixedly connected with one end of a second rotary connecting rod, another end of the second rotary connecting rod is rotatably connected with a connecting seat through a third pin shaft to form a third revolute pair, a rotation axis of the third revolute pair and an axis of the sliding sleeve are configured to be perpendicular to each other, and the connecting seat is fixedly connected with a connecting hole of the connecting holes in the distal fixation ring through a bolt and a nut.

6. The freely-connectable three-strut parallel orthopedic external fixator according to claim 5, wherein the first scale mark of the guide rail and the first indicating mark of the slider are configured in the form of a caliper; wherein the first scale mark corresponds to a main scale of the caliper, and the first indicating mark corresponds to an auxiliary scale of the caliper.

7. The freely-connectable three-strut parallel orthopedic external fixator according to claim 5, wherein the sliding sleeve is provided with third scale marks which are circumferentially spaced apart at the same angular intervals, and a third indicating mark is provided on the driving nut; when rotating the driving nut, a position indicated by the third indicating mark on the third scale marks continuously varies with a rotation angle of the driving nut, and a rotation amount α of the driving nut is read, a value of α ranges $0 \leq \alpha \leq 360°$; the displacement value of the second driving joint is calculated according to the following formula:

$$P_2 = l_2 + \alpha \cdot P_h / 360°$$

where $P_2$ represents the displacement value of the second driving joint, $l_2$ represents the displacement value of the second driving joint by rounding down the reading made by the second scale mark and the second indicating mark of the second driving joint, $P_h$ represents a thread lead of screw rod, and a represents the rotation amount of the driving nut.

8. The freely-connectable three-strut parallel orthopedic external fixator according to claim 7, wherein the driving nut is provided with a locking screw for pressing against the sliding sleeve.

9. The freely-connectable three-strut parallel orthopedic external fixator according to claim 2, wherein the sliding sleeve is provided with third scale marks which are circumferentially spaced apart at the same angular intervals, and a third indicating mark is provided on the driving nut; when rotating the driving nut, a position indicated by the third indicating mark on the third scale marks continuously varies with a rotation angle of the driving nut, and a rotation amount α of the driving nut is read, the value of α ranges $0 \leq \alpha \leq 360°$; a displacement value of the second driving joint is calculated according to the following formula:

$$P_2 = l_2 + \alpha \cdot P_h / 360°$$

where $P_2$ represents the displacement value of the second driving joint, $l_2$ represents the displacement value of the second driving joint by rounding down the reading made by the second scale mark and the second indicating mark, $P_h$ represents a thread lead of screw rod, and α represents the rotation amount of the driving nut.

10. The freely-connectable three-strut parallel orthopedic external fixator according to claim 9, wherein the driving nut is provided with a locking screw for pressing against the sliding sleeve.

11. The freely-connectable three-strut parallel orthopedic external fixator according to claim 6, wherein the sliding sleeve is provided with third scale marks which are circumferentially spaced apart at the same angular intervals, and a third indicating mark is provided on the driving nut; when rotating the driving nut, a position indicated by the third indicating mark on the third scale marks continuously varies with a rotation angle of the driving nut, and a rotation amount a of the driving nut is read, the value of α ranges $0 \leq \alpha \leq 360°$; the displacement value of the second driving joint is calculated according to the following formula:

$$P_2 = l_2 + \alpha \cdot P_h / 360°$$

where $P_2$ represents the displacement value of the second driving joint, $l_2$ represents the displacement value of the second driving joint by rounding down the reading made by the second scale mark and the second indicating mark of the second driving joint, $P_h$ represents a thread lead of screw rod, and α represents the rotation amount of the driving nut.

12. The freely-connectable three-strut parallel orthopedic external fixator according to claim 11, wherein the driving nut is provided with a locking screw for pressing against the sliding sleeve.

* * * * *